United States Patent [19]
Fawcett et al.

[11] Patent Number: 5,945,280
[45] Date of Patent: Aug. 31, 1999

[54] METHOD FOR DETECTION OF POLYNUCLEOTIDE HYBRIDIZATION

[75] Inventors: Newton C. Fawcett; Jeffrey A. Evans, both of Hattiesburg; Naomi Flowers Campbell, Collins, all of Miss.

[73] Assignee: The University of Southern Mississippi, Hattiesburg, Miss.

[21] Appl. No.: 08/486,933

[22] Filed: Jun. 7, 1995

Related U.S. Application Data

[60] Division of application No. 07/392,734, Aug. 11, 1989, Pat. No. 5,595,908, which is a continuation-in-part of application No. 07/253,906, Oct. 6, 1988, abandoned, which is a continuation of application No. 06/780,615, Sep. 26, 1985, abandoned.

[51] Int. Cl.$^6$ .............. C12Q 1/68; C12M 1/00; C07H 21/04; G01N 15/06
[52] U.S. Cl. .............. 435/6; 435/287.2; 536/24.3; 422/68.1
[58] Field of Search .............. 435/6, 287.2; 422/68.1, 422/69; 536/23.1, 24.3–24.33; 935/2, 3, 5, 76, 77, 78, 85; 436/501, 503, 94, 806

[56] References Cited

U.S. PATENT DOCUMENTS

| | | | |
|---|---|---|---|
| 4,242,096 | 12/1980 | Oliveira et al. | 23/230 B |
| 4,672,111 | 6/1987 | Haley et al. | 536/29 |
| 4,847,193 | 7/1989 | Richards et al. | 435/6 |

OTHER PUBLICATIONS

Kathryn Ann Drozda, "The use of Hybridization, Piezoelectric Crystals and Recombinant DNA Technology in the Detection of *Salmonella typhimurium*", masters thesis, University of Southern Mississippi Aug. 1985.

Sommer and Tautz, *Nucleic Acids Research*, vol. 17, No. 16, 1989, p. 6749.

"Characterization and Clinical Identification of Enterobacteriaceae by DNA Hybridization" by Don J. Brenner, Ph.D., Progress and Clinical Pathology, 1978, Chapter 4.

Sambrook et al., Molecular Cloning a Laboratory Manual, Second Edition, Cold Spring harbor Laboratory Press, pp. 9.47–9.52, 1989.

*Primary Examiner*—Bradley L. Sisson
*Attorney, Agent, or Firm*—Arnold, White & Durkee

[57] ABSTRACT

A method for detecting polynucleotide hybridization is disclosed. A polynucleotide is immobilized on a surface of a piezoelectric crystal. The resonance frequency of the piezoelectric crystal is measured through means for determining the resonant frequency of a piezoelectric crystal. A separate source of polynucleotide is exposed to the polynucleotide-coated piezoelectric crystal for a sufficient length of time and under conditions suitable for hybridization. The resonance frequency of the crystal is then again measured, and the difference between the resonance frequency before and after the incubation period will indicate the extent of hybridization.

17 Claims, 2 Drawing Sheets

METHOD FOR DETECTION OF POLYNUCLEOTIDE HYBRIDIZATION

This is a divisional of U.S. patent application Ser. No. 07/392,734 filed Aug. 11, 1989, issued Jan. 21, 1997 as U.S. Pat. No. 5,595,908, which is a continuation-in-part application of U.S. patent application Ser. No. 07/253,906 filed Oct. 6, 1988, now abandoned, which is a continuation of U.S. patent application Ser. No. 06/780,615 filed Sep. 26, 1985, now abandoned.

This invention was made with Government support under Contract DAAG29-84-K-0118, awarded by the U.S. Army Research Office. The Government has certain rights in this invention pursuant to 35 U.S.C. §202.

BACKGROUND OF THE INVENTION

The present invention generally concerns a system for detecting polynucleotide hybridization. More particularly, the invention pertains to a system for detecting polynucleotide hybridization utilizing piezoelectric crystals. The invention has particular application to medical diagnosis, bacteriology, virology, pathology, and biochemical and molecular biological research. For example, the system of the present invention is useful for detecting polynucleotide hybridizations such as DNA-RNA, DNA-DNA and RNA-RNA hybridizations.

DNA and RNA are strands of nucleic acids characterized by a phosphodiester link between the 3' position of one nucleic acid residue with the 5' position of the next nucleic acid residue. Nucleic acids contain one or more of the following bases: guanine (G), cytosine (C), adenine (A), and either thymine (T) (occurring in DNA) or uracil (U) (occurring in RNA).

In double-stranded DNA it is known that the pairing of the DNA strands are complementary, i.e., the guanine of one strand always pairs with the cytosine of the other strand (G-C), and the adenine of one strand always pairs with the thymine of the other strand (A-T). The same is true for double stranded RNA with the exception that uracil is substituted for thymine (A-U).

Pairing of single strands of polynucleotides occurs through hydrogen bonds formed between complementary bases of the nucleic acids. When heated sufficiently, the paired polynucleotides will melt; i.e., the hydrogen bonds are disrupted and the double strands are separated into individual strands (denatured). The polynucleotide strands tend to re-form duplexes once separated into singlestrands through the reforming of hydrogen bonds between complementary bases.

The ability of DNA or RNA strands to reanneal with complementary strands of polynucleotides has led to the ability to determine base sequence homology through hybridization. The extent of hybridization between a DNA strand with a known base sequence, for example, and a strand of polynucleotide from a different source, can serve as a measure of species relatedness, and is useful for the purpose, among others, of identifying bacteria and viruses.

Several methods of detecting polynucleotide hybridization have been developed. One such method of detecting polynucleotide hybridization relies on radiolabeling. Other known methods make use of renaturation rates, electron microscopic determination, and the use of fluorochrome labeled polynucleotides in conjunction with fluorescence microscopy. IgG specific for RNA:DNA hybrids has also been used. Still other methods use nucleotide derivatives which contain biotin, aminobiotin, lipoic acid and other determinants attached covalently to the pyrimidine or purine ring.

The techniques employed for detecting DNA or RNA relatedness have been applied in research laboratories for several purposes, such as identifying biochemically atypical strains, classifying poorly studied groups of organisms, justifying or invalidating proposed taxonomic changes, determining the relationships between newly described organisms and existing taxons, and for identifying mixed cultures. Unfortunately, the application of these techniques in clinical studies have for most purposes been impractical. For example, in clinical studies where DNA hybridization detection employs radiolabeling, the technique has been shown to be impractical since it lacks simplicity and rapidity, is expensive, and poses potential safety hazards.

SUMMARY OF THE INVENTION

Generally, the present invention comprises a novel component and method for the detection of polynucleotide hybridization. A polynucleotide is immobilized on a surface of a piezoelectric crystal and the resonance frequency of the crystal is then noted. A variety of means for determining the resonance frequency of a piezoelectric crystal can be employed. Polynucleotide hybridization can then be detected by measuring the difference between the resonance frequency of the piezoelectric crystal before and after the prepared crystal is exposed to a separate source of polynucleotide under suitable hybridization conditions.

DETAILED DESCRIPTION AND PREFERRED EMBODIMENT

Piezoelectric Detection of Mass

Piezoelectricity is the electricity, or electric polarity, resulting from the application of mechanical pressure on a dielectric crystal. The concept of piezoelectricity is well known. For example, piezoelectric crystals are used in controlling frequencies in the communications field, as selective filters in electronic networks and also as sensors to accurately measure temperature.

Certain crystals exhibit a piezoelectric effect, i.e., compression of the crystals generate an electrostatic voltage across the crystals. Examples of these types of crystals include quartz, ethylene diamine tartrate, barium titanate, zincblende and the like. The frequency of a crystal depends on its effective mass. The resonant frequency of the crystal can be obtained with a frequency meter attached to the output of an oscillator circuit. If the mass of the crystal is altered, as for example, by adding material to the surface of the crystal, the resonant frequency of the crystal will change and can be measured on a frequency meter. The frequency of the crystal will lower proportionally to the amount of mass added to the crystal.

Piezoelectric crystals are commonly produced from AT or BT cut quartz plates (AT and BT refer to the orientation of the plate with respect to the crystal structure). AT and BT cut crystals vibrate in a shear mode about an axis parallel to the major surface, and have low or zero temperature coefficients at the temperature of use. The AT cut is superior to the BT cut in temperature coefficient and mass sensitivity. A typical 9 MHz crystal is a 10–16 mm disc, square or rectangle about 0.15 mm thick. A 9 MHz, AT cut quartz crystal has proven very effective in the practice of this invention.

Means for detecting the resonance frequency of a crystal can be provided in a variety of ways. Generally, a crystal will be interposed between electrode material, the leads of which are connected to an oscillator circuit. A frequency meter or the like attached to the output of the oscillator circuit is used to measure the resonance of the crystal.

The electrode material need not be in physical contact with the crystal. However, an efficient way of preparing a piezoelectric crystal for use in the present invention is to deposit electrode material on opposite surfaces of the crystal. For example, on a typical quartz crystal, the electrode material can be deposited on the central region of opposing crystal surfaces. In addition, a band of electrode material can be deposited on the crystal surface to form a pathway from the electrode material deposited on the central region of crystal surface to the edge of the crystal where leads for connecting to an oscillator circuit can be attached.

Any suitable electrode material can be used in the practice of this invention. Such materials include, but are not limited to, gold, silver, aluminum, nickel, chromium, titanium tantalum and the like.

The instrumentation employed, such as a simple oscillator circuit, a frequency counter and a vacuum oven, and the use of micro-electric circuitry should be economically advantageous since it is inexpensive yet effective. In addition, the present invention should require only limited training to operate, especially since a signal from a piezoelectric crystal is at a frequency which can easily be displayed on a digital meter or converted to a digital signal for communication to a computer.

Bonding of Polynucleotides to Piezoelectric Crystals

It is well known that polynucleotides will hybridize. For example, denatured DNA plus its complement will hybridize under the proper conditions and reassociate into double-stranded DNA. Hybridization of a DNA strand occurs only if incubated with its complement. Partial hybridization can occur between single strands of related species. The extent of hybridization corresponds to the extent of species relatedness. For example, hybridization of approximately 60% is considered to indicate a close relation between species.

Polynucleotides can be chemically bonded directly to a piezoelectric crystal surface or indirectly via a material previously deposited on the crystal surface. The crystal surface, for the purposes of this description, includes the crystal surface per se or any material or materials deposited on the surface of the crystal. Such other material can be electrode material or a thin layer of polymeric or other bonding material, such as intermediate molecule links. For example, a synthetic polynucleotide can be bonded chemically to the crystal surface to which a second, naturally occurring, polynucleotide can be attached by enzymatic ligation. More particularly, a polynucleotide can be ligated by enzymatic reaction (DNA or RNA ligase) to a different polynucleotide which is covalently bonded by chemical reaction to a functional group which is in turn chemically bonded to a substrate, for example, a polymeric substrate.

Particularly effective polymeric substrates are those polymers characterized by hydrolytically stable, hydrophobic backbones substituted with reactive pendant groups. For example, such polymers include, but are not limited to, copolymers of ethylene or propylene and N-(6-x-hexyl)-acrylamide, copolymers of styrene and p-x-methyl styrene, copolymers of alkylated siloxanes and 6-x-hexyl and alkyl substituted siloxanes, and similar polymers where x is, a reactive group such as amino, sulfhydryl, iodo, bromo, chloro, carboxyl, hydroxy, chloro carbonyl, dimethylsilyl and similar groups which are capable of combining with polynucleotides or derivatized polynucleotides. Other polymers useful in the present invention include, but are not limited to, poly(butyl methacrylate), polyurethane and the like.

One of the most sensitive areas for immobilizing the polynucleotides is the central portion of the crystal surface.

In one embodiment of the present invention a polymer solution (usually 5 to 15 $\mu l$) is pipetted onto the crystal and the solvent is evaporated in vacuo. Depending upon the polymer solution used and prior experience, the crystal may be washed at this stage. The wash may consist of a combination of solvent or solvents and solutions. A typical wash would be with 100 ml of distilled water. As described above, it may be desirable to attach the polynucleotides to that portion of the crystal surface comprising the electrode material. In this instance, the polymer can be applied substantially to that area of the crystal surface.

The resonance frequency of the dry crystal can be optionally measured at this stage. If this is done, washing followed by drying in vacuo and measurement of the resonance frequency should be repeated until the resonance changes by less than +/−50 Hz between successive wash-dry cycles. Prior experience may indicate the amount of washing required to achieve a stable frequency (+/−50 Hz) at this stage. Indeed, prior experience may indicate that no wash-dry cycle is required at this point. Whether a wash cycle is needed will largely be determined by the polymer and attachment method used. The reverse side of the crystal may optionally be treated in the same way.

A buffer solution (usually phosphate buffer, pH=6 to 8) containing the polynucleotide to be immobilized is pipetted onto the crystal surface. This solution may contain additional linking reagents which react with either the polynucleotide, or with the polymer, or with both, to form chemical bonds between the polynucleotide and the polymer or other surface material. In some cases these reagents that can react with the polynucleotide, or with polymer, or with both may be applied to the crystal and dried before polynucleotide addition. Alternatively, electromagnetic radiation may be used to activate preexisting functional groups on the polymer or the polynucleotide, or both, to cause formation of chemical bonds between the polynucleotide and the substrate.

After reaction with DNA or RNA, the crystal is repeatedly washed with distilled water and dried in vacuo until the resonance frequency is stable within +/−50 Hz. The temperature of the wash may be elevated, but not so high as to cause hydrolysis or other disruption of desirable bonds.

After the desired polynucleotide has been coated on the crystal surface, the crystal frequency can be recorded. This is done first by washing the crystal of all soluble and nonadhering material, and then drying the crystal in a vacuum under low heat. Afterwards, the resonance frequency of the crystal is measured and recorded.

The piezoelectric crystals, nucleic acids and other polymers used are relatively stable and inexpensive. It is contemplated that prepared piezoelectric crystals can be manufactured so inexpensively that one-time use will be feasible. Thus, one distinct advantage of the present invention is the ability to provide a variety of kits for use in the detection of polynucleotide hybridization. For example, such kits can include, as separate components, a test crystal, a control crystal, polymer, polynucleotide, linking reagent, electronic equipment, or any combination of these. In addition, the kit can include the crystal prepared to any extent desired, for example, with the polymer or other substrate or linking material only, or with the polynucleotide attached.

Piezoelectric Detection of Hybridization

An aqueous buffer solution containing a polynucleotide is deposited on the surface of the crystal prepared generally as described above. The polynucleotide in the solution can be either single- or double-stranded. The solution and crystal can be heated to a temperature sufficient to melt any double-stranded polynucleotides to single strands. Next, the temperature is brought to a predetermined value optimum for the hybridization of the reference polynucleotide. This incubation period is allowed to continue for a predetermined amount of time based on the polynucleotide involved. This period can last from a few minutes to several hours depending on the complexity of the polynucleotide.

In one embodiment, hybridization is carried out by incubating on the surface of a crystal a buffered solution of polynucleotide. Typically the solution will contain about 1 mg/ml of the polynucleotide to be tested, but can have a substantially lower concentration. A typical incubation temperature would be approximately 30° C. below the melting temperature of the duplex to be formed. The incubation time will vary from a few minutes to several hours depending upon the complexity and molecular weight of the polynucleotide to be duplexed. A useful temperature regimen involves heating the polynucleotide solution above its melting point and applying the hot solution to the crystal. Then the temperature is lowered to the incubation temperature and held there for the required time. Alternatively, a melted solution of DNA or RNA can be rapidly cooled, i.e., quick cooled, to slow the spontaneous association of complementary DNA or RNA strands.

The quick cooled solution is then applied to the crystal and incubated at the optimum temperature for duplex formation. In many cases it is possible to use solvent systems which lower the association temperature. For example, use of 50% formamide allows effective incubation at lower temperatures in cases where an elevated temperature would be required without formamide.

Typically 1 to 50 $\mu$l of polynucleotide solution is applied to one or both sides of the crystal. The solution should be retained on the crystal during incubation without significant evaporation. This can be done, for example, by forming a silicone rubber reaction chamber (dome) over the crystal's central region. The reaction chamber can be made from a silicone gas chromatograph septum with the center portion removed and covered with a second intact septum. Alternatively, a reaction chamber specially manufactured to accommodate piezoelectric crystals can be used.

Following the incubation period, the crystal is washed free of soluble and nonadhering material and dried under a vacuum. If the applied solution contained a polynucleotide which is the complement of the reference polynucleotide, then the mass of polynucleotide on the crystal surface should be increased. Generally, the reference polynucleotide will be immobilized on the crystal surface prior to incubation with the test polynucleotide. However, it is possible to reverse this order, i.e., immobilize the test polynucleotide on the crystal surface and then incubate the crystal with the reference polynucleotide.

This system is capable of providing both qualitative and quantitative detection of hybridization. The amount of the increase in mass caused by hybridization of the polynucleotides is generally measured with a frequency meter. The extent of hybridization is evaluated from the difference in resonance frequency before and after the incubation step. For example, based on a 9 MHz crystal, an approximately 0.8 hertz shift corresponds to a one nanogram change in mass. The sensitivity of the detection is a function of the fundamental frequency of the crystal. A higher fundamental frequency of the crystal corresponds to an increase in sensitivity, while a lower fundamental frequency will give the opposite result.

In another preferred embodiment, measurement of hybridization of target sequences with probe sequence attached to a piezoelectric crystal can be achieved in the liquid phase. Crystals prepared by the methods of the invention and to which are attached a probe sequence are equilibrated in the presence of a small volume of a buffer on the crystal's surface. Following equilibration, target sequence polynucleotide can be added to the buffer in a small volume. Hybridization of the two sequences can be monitored in the liquid phase over time without a need for drying the crystalline surface. In so doing, it is possible to follow hybridization of two sequences over time and to distinguish hybridizing from non-hybridizing sequences in the liquid phase.

In yet another preferred embodiment, it is possible to reutilize the crystals to which are attached a probe polynucleotide. Since the chemistry of nucleic acids allows melting of hybridized pairs of sequences at certain elevated temperatures, treatment with elevated temperatures of crystalline surfaces to which probe polynucleotide sequences are attached may be used to remove any polynucleotide which has hybridized to the probe sequence.

The ability of the crystalline components of the invention to be used at elevated temperatures is unique and allows re use of the component. Furthermore, the crystals used in this manner provide a technique for measurement of the melting process of nucleic acid hybrids. By taking advantage of this capability, it is possible to measure the homology of two DNA single stranded sequences by monitoring the melting using the invention.

In addition, it is contemplated that this system will provide numerous advantages over other known techniques, especially in clinical work where rapid and accurate, yet economically obtained, results are required. The subject invention provides faster results due to the basic simplicity of piezoelectric mass detection and can be applied to mixed bacterial or viral cultures whereas non-hybridization methods of identifying bacteria and viruses generally require that a pure culture (non-mixed) be obtained. In addition, the present invention should provide an advantage over older methods of pathogen identification. The older methods are based on the observation of phenotypes which can fail to correctly identify mutated species which can otherwise be detected by hybridization techniques. Moreover, mutagenic dyes, as used in fluorescence assay methods, and $^{32}$P or equally hazardous isotopes, as used in radio assay methods, are avoided.

Other diagnostic uses are also contemplated as being within the scope of the present Invention. For example, it is contemplated that the present invention will be useful for diagnosing the presence of nucleic acid-containing etiological agents, testing bacterium to determine the presence of resistance to an antibiotic, detecting genetic disorders, diagnosing tumor cells and other similar techniques where polynucleotide hybridization is employed.

The following examples are given to more fully illustrate the present invention, and shall not be construed as limiting the scope of the invention in any way. These examples are representative of the immobilization of polynucleotides on crystals, their subsequent hybridization and the detection of hybridization by their piezoelectric resonance. Therefore, the method is not limited to only those DNAs or RNAs enumerated.

EXAMPLES

The procedures used in the following Examples follow the general procedures discussed above. The procedures were carried out in parallel on two separate crystals, one of which was designated as a control. The frequency shifts obtained upon hybridization are expressed relative to the control.

The control was processed in the same manner as the test sample except that the conditions for the control were adjusted so that significant hybridization would not occur.

The results are expressed as follows:

$$\Delta HZ = (Hz_2 - Hz_3)_{control} - (Hz_2 - Hz_3)_{test\ sample}$$

where:

$Hz_2$ = the resonance frequency of the prepared crystal, and $Hz_3$ = the resonance frequency of the crystal following the incubation period.

Hybridization is generally indicated when ΔH has a value from minus a few hundred to minus several thousand Hertz. The reproducibility of ΔHz depends on various factors such as the reproducibility of the polynucleotide immobilization and the subsequent hybridization conditions and reactions.

RNA Hybridization Detected by Piezoelectric Resonance

It is well known that hybridization will occur between polyinosinic acid (poly I) and polycytidylic acid (poly C) to form a double-stranded synthetic polymer (poly I:C). However, hybridization will not occur between polyuridylic acid (poly U) and polyinosinic acid (poly I). Examples 1–3 below demonstrate the ability to measure specific hybridization which can occur on the crystal surface.

Example 1

Polycytidylic acid was hybridized with Polyinosinic acid attached to Poly(butyl methacrylate) substrate as follows:

10 μl of poly(butyl methacrylate) (0.1% in ethyl acetate) was applied to both sides of the crystal and dried. 10 μl of triazido trinitro benzene linker (0.1% in chloroform) was applied to both sides of the crystal. 5 μl of 1 mg/ml poly I in buffer A (0.14 Molar sodium phosphate, pH 6.8) was applied to both sides of the polymer coated crystal and irradiated at 300 nanometers for 30 minutes on each side. 5 μl of 1 mg/ml poly C in buffer A was applied for hybridization. Hybridization was done at 46° C. for 25 minutes under a glass dome.

The control crystal was carried through the identical procedure without polyinosinic acid FIRST RESULT: ΔHz=−613 versus control SECOND RESULT: ΔHz=−686 versus control

Example 2

Polycytidylic acid was hybridized with Polyinosinic acid attached to a polyurethane substrate as follows:

5 μl of polyurethane (0.2% in dimethylformamide) was applied to both sides of the crystal and dried. 5 μl of 2,6-bis(4-azidobenzylidene)-cyclohexanone linker (0.1% in acetone) was applied to both sides of the crystal. 5 μl of 5 mg/ml poly I in buffer B (0.10 Molar sodium, 0.01 Molar phosphate, pH 7.8) was applied to both sides of the polymer coated crystal and irradiated at 330 nanometers for 30 minutes on each side. 5 μl of $2.0 \times 10^{-3}$ Molar poly C (0.65 mg/ml) in buffer B was applied to both sides of the crystal for hybridization. The crystal was heated with poly C to 65° C. for 30 minutes and the hybridization was carried out at room temperature for 2 hours with silicone rubber domes.

The control crystal was carried through an identical procedure without polyinosinic acid.

RESULT: ΔHz=−1237 versus control

Example 3

Polycytidylic acid was hybridized with polyinosinic acid attached to a polyurethane substrate with cyclohexene reactive site mask as follows:

10 μl of polyurethane (0.2% in dimethylformamide) were added to both sides of the crystal and dried. 10 μl of 2,6-bis(4-azidobenzylidene)cyclohexanone linker (0.2% in acetone) was then added to both sides of the crystal. 5 μl of $2.0 \times 10^{-3}$ Molar poly I (0.70 mg/ml) in buffer B (0.10 Molar sodium, 0.10 Molar phosphate, pH 7.8) was applied to both sides of the polymer coated crystal and irradiated at 366 nanometers for 0.5 hours. 10 μl of cyclohexene was applied to each side of the crystal and irradiated at 366 nanometers for 10 minutes on each side. 5 μl of $2.0 \times 10^{-3}$ Molar poly C (0.65 mg/ml) in buffer B was applied to both sides of the crystal for hybridization. The crystal was heated to 60° C. with the poly C for 30 minutes and then incubated for 2 hours at room temperature for hybridization.

The control crystal was carried through the identical procedure, but using 5 μl of $2.0 \times 10^{-3}$ Molar polyuridylic acid (0.65 mg/ml) in place of polycytidylic acid.

RESULT: ΔHz=−227 Hz versus control

The control ($Hz_3 - Hz_2$) was +18 Hz demonstrating that there was no apparent hybridization between the polyinosinic acid immobilized on the crystal and polyuridylic acid present in solution. This is consistent with the known specificity of polyinosinic acid for hybridization to poly C but not to poly U.

DNA Hybridization Detected by Piezoelectric Resonance

Example 4

*Salmonella typhimurium* (*S. typhimurium*) DNA was hybridized to *S. typhimurium* DNA attached to a poly(butyl methacrylate) substrate as follows:

10 μl of a 100:1 (Volume/Volume) solution of poly(butyl methacrylate) (0.1% in ethyl acetate) and dimethoxyphenylacetophenone (0.1% in acetone) was applied to the crystal. 10 μl of 1 mg/ml *S. typhimurium* DNA (denatured by boiling and then quick cooling at 4° C.) in buffer A (0.14 Molar sodium phosphate, pH 6.8) was applied to one side of the crystal and irradiated at 365 nanometers for 2 hours. The crystal was rinsed with distilled water and dried. In the case of RESULT 1 below, an additional 10 μl of denatured *S. typhimurium* DNA was applied and irradiated as above. Hybridization was carried out with 10 μl of 1 mg/ml melted *S. typhimurium* DNA (heated at 100° C. and then cooled to 65° C.). Incubation was at 65° C. for 2 hours with a silicone rubber dome.

The control crystal was carried through the identical procedure but incubated with 20 μl of 0.4 mg/ml of melted calf thymus DNA instead of melted *S. typhimurium* DNA during the hybridization step.

FIRST RESULT: ΔHz=−779 versus control

SECOND RESULT: ΔHz=−1013 versus control

Example 5

*S. typhimurium* DNA was hybridized to *S. typhimurium* DNA attached to a poly(butyl methacrylate) substrate as follows:

10 μl of a 100:1 (Volume/Volume) solution of poly(butyl methacrylate) (0.1% in ethyl acetate) and dimethoxyphenylacetophenone (0.1% in acetone) was applied to the crystal. The crystal was then dipped into the poly(butyl methacrylate):dimethoxyphenylacetophenone solution having the above composition. 10 μl of 1 mg/ml *S. typhimurium* (denatured by boiling and then quick cooling at 4° C.) in buffer A (0.14 Molar sodium phosphate, pH 6.8) was applied to one side of the crystal and irradiated at 365 nanometers for 2 hours. Hybridization was carried out with 10 μl of 1 mg/ml melted *S. typhimurium* DNA (heated at 100° C. and then cooled to 65° C.) and incubated for 2 hours with a silicone rubber dome.

The control crystal was carried through the identical procedure, but denatured calf thymus DNA (25 pl of 0.4 mg/ml in buffer A) was used for immobilization instead of denatured *S. typhimurium* DNA.

RESULT: ΔHz=−833 versus control

Example 6

*S. typhimurium* DNA was hybridized to endonuclease restricted *S. typhimurium* DNA inserted into single-stranded M13 viral DNA attached to poly(butyl methacrylate) as follows:

5 μl of a 100:1 (Volume/Volume) solution of poly(butyl methacrylate) (0.1% in ethyl acetate) and dimethoxyphenylacetophenone (0.1% in acetone) was applied to the crystal. 10 μl of 1 mg/ml single-stranded M13 mp8 with Salmonella DNA insert in buffer B (0.10 Molar sodium, 0.10 Molar phosphate, pH 7.8) was applied to a polymer coated crystal and irradiated at 365 nanometers for 2 hours. 10 μl of 1 mg/ml blender sheared (4 minutes), melted *S. typhimurium* DNA was applied for hybridization at 65° C. for 2 hours using silicone rubber domes.

Control 1: The crystal was carried through an identical procedure but using 10 μl of 1 mg/ml of blender sheared, melted calf thymus DNA for the hybridization step instead of *S. typhimurium* DNA.

Control 2: The crystal was carried through an identical procedure, but using buffer B instead of M13 mp8 DNA with Salmonella DNA insert, and using 10 μl of 1 mg/ml blender sheared, melted calf thymus DNA for the hybridization step instead of *S. typhimurium* DNA.

RESULT: ΔHz=−557 versus control 1

ΔHz=−875 versus control 2

Example 7

AT cut, 9 MHz crystals with gold electrodes were prepared by rinsing with water followed by rinsing with acetone. The polymer polymethylmethacrylate methylacrylic acid (2 g/l in acetone) was applied using an airbrush. A sufficient quantity of the polymer was applied to both sides of the crystal to bring about a net change in resonance frequency of 2,800 to 10,300 Hz as compared to the untreated crystal. The crystals were then placed in an oven at 110° C. for 15 hours, removed and allowed to cool for approximately 20 minutes.

Polyadenylic acid (Poly A) and adenosine monophosphate (AMP) probes were attached to the polymer surface by using a carbodiimide coupling reaction. The carbodiimide reagent was prepared by dissolving 14.5 mg of solid carbodiimide in 250 μl of carbonylimidazole buffer (100 mM carbonylimidazole in distilled water, pH 6.0). Approximately 20 μl of the resulting carbodiimide solution was applied to the center of the crystal and allowed to set for 1.0 minute. The carbodiimide solution was then removed by suction and 20 μl of poly A or AMP probe (each in a solution of 36 mg/ml in 0.14 M phosphate buffer, pH 6.7) were applied to the crystal. The probe solution was allowed to remain in contact with the crystal for approximately 2.5 hours, removed and the crystal surface was rinsed three times with 20 μl of cold water and allowed to air dry. During each step of the above procedure, frequency readings were taken. The results of such a series of frequency readings for 4 crystals are shown in the table below.

| Crystal Number | 77 | 78 | 79 | 90 |
|---|---|---|---|---|
| Starting Frequency | 9034566 | 9025518 | 9032641 | 9030648 |
| Decrease in Frequency Due to Polymer Application | −10320 | −8809 | −8641 | −2795 |
| Probe Applied | poly A | poly A | poly A | AMP |
| Decrease in Frequency Due to Probe Attachment | −1518 | −1671 | −1541 | −188 |
| Target Applied | poly U | poly A | poly U | poly U |

In order to measure hybridization of target sequences with probes in the liquid phase, the crystals prepared as above were connected to an oscillator circuit and a frequency counter which was controlled by computer through a general purpose interface bus. Frequency recording was initiated and allowed to stabilize for approximately 2 minutes prior to placing 20 μl of phosphate buffer (0.14 M pH 6.7) onto the crystal. The crystal's resonance frequency was again allowed to stabilize for approximately 21 to 22 minutes prior to addition of 1.0 microliter of target. Frequency readings were continued for 45 minutes to 1.0 hour. Preferably, five frequency readings were averaged for each data point collected, producing an acquisition rate of approximately 10 points per minute. During the frequency measurements, the operation of the oscillator circuit was repeatedly checked against a reference crystal in order to ascertain that circuit drift is negligible and that the circuitry is functioning properly. Variation in the reference crystal frequency should be no greater than approximately 0.2 ppm.

Figure 1:
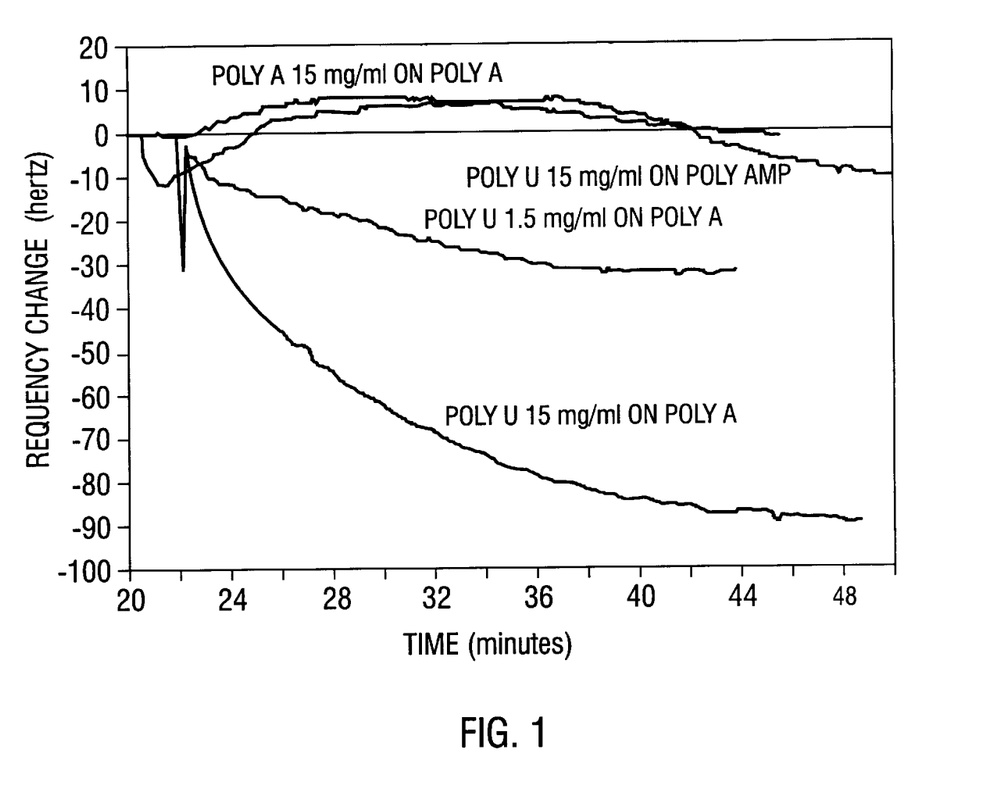
FIG. 1—From top to bottom: (1) crystal 90 with AMP probe and poly U target; (2) crystal 78 with poly A probe and poly A target; (3) test crystal with poly A probe and 1 μl of 1.5 mg/ml poly U target; (4) test crystal with poly A probe and 1 μl of 15 mg/ml poly U target.

Results of a study utilizing the crystals, probes and target sequences listed in the table above are shown in FIG. 1. FIG. 1 shows a recording for various probes and targets of the change in resonance frequency over time. The two upper curves correspond to the crystals 78 and 90 and represent different non-hybridizing controls. Crystal 78 has poly A probe and poly A target and, therefore, shows no significant alteration of resonance frequency. Crystal 90 has AMP probe and poly U target and similarly shows no significant hybridization. The frequency change after 45 minutes of hybridization for such controls should be approximately 10 Hz or lower.

The next lower curve is that for the hybridization of poly A probe and 1.0 microliter of 1.5 mg/ml of poly U target. After 45 minutes, this crystal demonstrated a frequency change of approximately 35 Hz. The lowest curve is that for poly A and 1.0 microliter of 15 mg/ml poly U target. After 45 minutes, this increased concentration of target nucleic acid showed a frequency drop of approximately 90 Hz.

As can be seen from the preceding example, it is possible to distinguish hybridizing from non-hybridizing sequences in the liquid phase. More importantly, however, this example demonstrates the capability of the invention to electronically monitor ongoing hybridization in the liquid phase without the need for drying.

Example 8

Poly uridylic acid (poly U) was hybridized to poly adenylic acid (poly A) previously attached by nitrene insertion reaction to polymethyl methyacrylate:methyl acrylic acid copolymer (75:25) (PMMA-MAA) coated quartz crystals. The hybridization of the poly A coated crystals was carried out in repeated cycles of hybridization and melting. The processes involved are described below.

Process 1. Poly A containing both adenosine monophosphate (AMP) and 8-azido AMP units was prepared from adenosine diphosphate (ADP) and 8-azido ADP by incubation with polynucleotide phosphorylase in the following manner.

In a 0.5 ml volume the starting solution contained 50 mM Tris-Cl, pH 9.6, 5 mM $MgCl_2$, 0.3 mM $Na_2EDTA$ pH 7.4, 0.1 mg bovine serum albumin, 5–7 micromoles of ADP, and 5 units of polynucleotide phosphorylase (*E. coli*, Sigma Chemical Co.). This solution was incubated for approximately 32–48 hours at 37° C. Then 5 micromoles of 8-azido ADP was added to the solution. In some cases, additional micromoles of ADP can be added to the solution. The solution was then incubated approximately an additional 12–24 hours. The solution was then diluted with 0.33 ml of water and extracted 2 times with 5:3 chloroform:isoamyl alcohol and 1 time with ether. The aqueous layer was applied to a Sephadex G-50 column and eluted with 0.5 M NaCl. The solution eluting in the void volume of the column was precipitated with ethanol and was redissolved in 0.14 M sodium phosphate buffer, pH 6.7. The resulting solution contained poly A with both AMP and 8-azido AMP units and was referred to as azido poly A.

Process 2. Attachment of azido poly A to 75:25 PMMA-MAA coated crystals was accomplished in the following manner.

The crystal's gold electrode was coated with PMMA-MAA copolymer by spraying with a solution of 0.1% PMMA-MAA in acetone. After measurement of the resonance frequency of the crystal a 10 microliter aliquot of the azido poly A (2.4 mg/ml (or less) in 0.14 M phosphate buffer, pH 6.7 was placed on the polymer coating and allowed to evaporate to near dryness in the dark. The crystal was then placed on the surface of a 300 nm UV transluminator and irradiated for 10 minutes. The crystal was then rinsed with cold sterile water (5×30 microliter rinses) and the frequency was measured after drying. A decrease in frequency was observed indicating attachment of the azido poly A to the crystal. Controls in which no UV irradiation or in which poly A without azido groups was used showed little or no frequency change. This indicated the azido poly A attached to the polymer coated crystals primarily through the activation of the azido group to a nitrene followed by its insertion into the polymer coating. In some cases the crystals used for attachment of azido poly A had previously gone through the attachment of azido poly A, as above, and hybridization with poly U, as below, before apparent stable attachments were achieved. Apparently this "precycling", which involves heating at 65° C. and rinsing, removes loosely adhering material and therefore subsequent azido poly A attachments appear more stable.

Process 3. Hybridization of poly U to the poly A was carried out in the following manner.

A crystal with attached poly A was preincubated with 10 μl of 0.14 M sodium phosphate, pH 6.7, at 65° C. for 5 minutes. Excess buffer was removed and a 10 microliter aliquot of a 1 mg/ml solution of poly U in 0.14 M sodium phosphate, pH 6.7, at 65° C. was applied to the crystal's surface. After 10 minute incubation at 65° C. the crystal was allowed to cool to room temperature and incubated for at least 1 hour (typically 2 hours) at room temperature. The crystal was kept under high humidity during the entire process. The crystal was then rinsed with 30 microliter portions of 4° C. water until reaching a stable frequency after drying. Controls were run with crystals that had no poly A attached or that were incubated with 10 microliter of 1 mg/ml of poly cytidylic acid (poly C) in 0.14 M sodium phosphate, pH 6.7, which is not complementary to poly A.

Process 4. Cycles of poly U hybridization and melting were carried out in the following manner.

After the frequency change of the crystal was measured following poly U hybridization in process 3 above, the crystal was rinsed 5 times with 30 μl of 0.14 M sodium phosphate, pH 6.7, at 65° C., 10 times with 30 μl of water at 65° C., and finally with 30 microliter aliquots of 4° C. water until a stable frequency was obtained. After this melting process, the crystal was ready for rehybridization with poly U as in process 3 above. Results:

Three crystals, A, B, and C were carried through processes 2 and 3 above as a precycling procedure. After the precycling, the frequency was measured and termed the "Initial Hz." Then the azido poly A was reapplied to the crystals' surfaces (step 1 below). The crystals were then subjected to the different steps indicated in the table below. The frequency of each crystal was measured in the dry state at the end of each step. Crystal A is the crystal on which hybridization was anticipated, while crystals B and C are controls. Frequencies in the table, from step 1 through 11, are expressed relative to the crystal's "Initial Hz" before the step 1 attachment of azido poly A below.

| ATTACHMENT OF POLY A AND HYBRIDIZATION WITH POLY U | | | |
|---|---|---|---|
| | | Frequency in Hertz (Hz) | |
| | crystal A | B | C |
| Initial Hz (before Poly A) | 9038044 | 9041270 | 9040231 |
| | Frequency Change in Hz (Hz after each step - Initial Hz) | | |
| | crystal A | B | C |
| Step 1: Attachment of azido Poly A | | | |
| UV irradiated | −2257 | −1750 | |
| no UV irradiation | | | −3 |
| Step 2: Hybridization test with | | | |
| A. Poly U | −3565 | | −18 |
| B. Poly C | | −1664 | |

These steps demonstrated that the azido poly A can be attached to the polymer coated crystals (step 1: crystals A &

B) in the presence of UV irradiation. Without UV treatment, little attachment occurred (step 1: crystal C). In the hybridization test, when poly U was used (step 2), a further decrease in frequency of 1,308 Hz (3565−2257=1308) was observed relative to the crystal after attachment of poly A (step 1; crystal A). An increase in frequency of 86 Hz was observed when poly C was used (step 2) relative to the crystal's frequency after attachment of poly A (step 1; crystal B). This demonstrated that the piezoelectric resonance method can detect specific nucleic acid hybridization.

As can be seen by examining the frequency changes in steps 3 through 11 in the table below, poly U addition to crystal A always resulted in further decrease in frequency of the crystal relative to the value after the poly A attachment in Step 1. In contrast, the incubation with noncomplementary poly C on crystal B did not lead to a further frequency decrease as compared to Step 1. Step 8 was another control in which the poly U was incubated with crystal B and which had previously shown no frequency decrease with poly C incubations. In this case, the poly U showed a further frequency decrease of over 1100 Hz relative to Step 7B. Furthermore, when crystal A was incubated with poly C, no further frequency decrease was observed (step 8A). These controls indicated that crystals A and B behaved similarly when incubated with poly U.

The melting steps in each case resulted in return of the frequency to slightly higher levels than before the corresponding hybridization step (e.g., compare Step 3A, before hybridization, with Step 5A, after hybridization and melting). This demonstrated that melting of nucleic acid double strands can be monitored by the piezoelectric resonance method.

The control crystal C, which had no poly A attached, did not demonstrate marked frequency changes on either the hybridization steps or the melting steps. This demonstrated that poly A must be attached to the crystal before hybridization with poly U can occur. The frequency of crystal C was not measured in steps 9–11.

CYCLING OF CRYSTALS

Frequency Change in Hz
(Hz after each step - Initial Hz)

| crystal | | A | B | C |
|---|---|---|---|---|
| Steps | | | | |
| 3: | Melting of hybrids | −1891 | −1610 | −129 |
| 4: | Hybridization with | | | |
| | A. Poly U | −3281 | | −139 |
| | B. Poly C | | −1541 | |
| 5: | Melting of hybrids | −1724 | −1453 | −155 |
| 6: | Hybridization with | | | |
| | A. Poly U | −3021 | | −251 |
| | B. Poly C | | −1380 | |
| 7: | Melting of hybrids | −1543 | −1113 | −152 |
| 8: | Hybridization with | | | |
| | A. Poly C | −1540 | | −158 |
| | B. Poly U | | −2273 | |
| 9: | Melting | −1470 | −975 | |
| 10: | Hybridization with | | | |
| | A. Poly U | −2773 | | |
| | B. Poly C | | −894 | |
| | (note return to normal poly U and poly C incubations) | | | |
| 11: | Melting | −1366 | −934 | |

Figure 2:
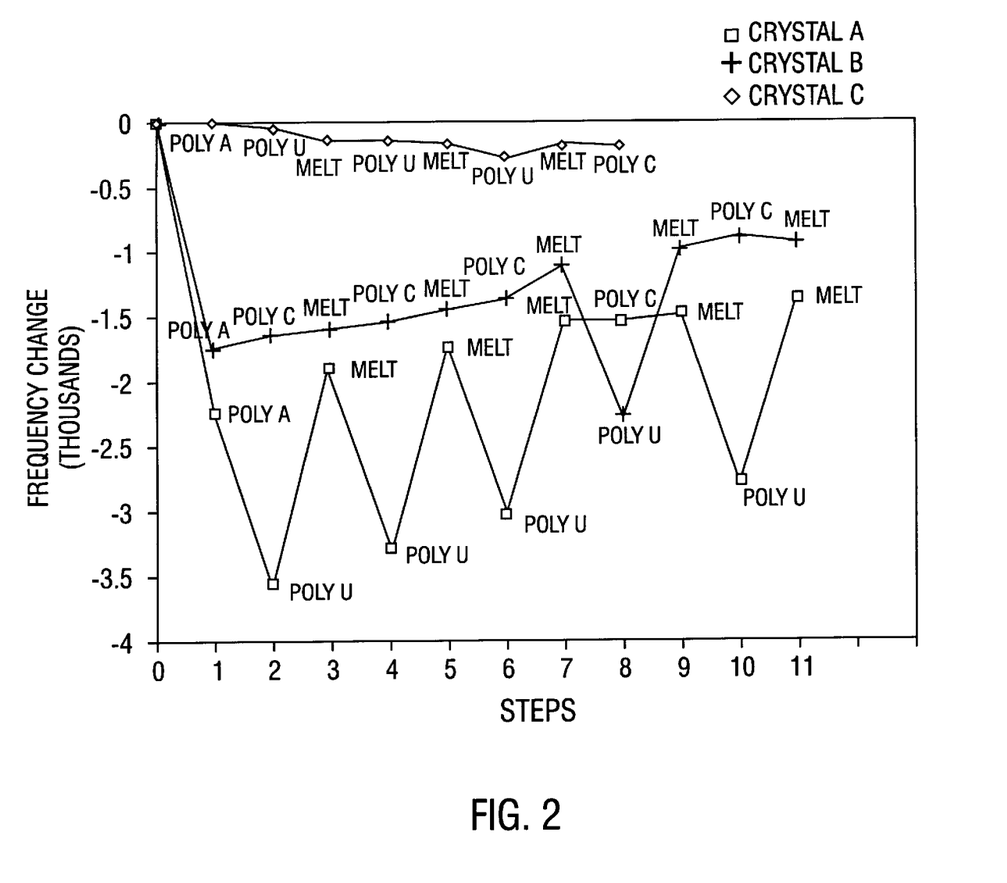
FIG. 2—The frequency changes are all expressed relative to the crystal's initial Hz before the attachment azido poly A. Each step on the x-axis corresponds to one of the steps in the table above. Each line on the graph represents the frequency changes accompanying the steps. The bottom line is crystal A, the middle is crystal B, and the top is crystal C. Each point is labelled, with poly A* representing the attachment reaction with azido poly A; poly U and poly C for their points of addition; and melt for the melting process.

The overall results demonstrated that the crystal with azido poly A attached could be reused or cycled for the detection of specific hybridization to poly U. At least 5 cycles of hybridization and melting were shown to be possible. A graphical view of steps 1–11 for crystals A, B and C is shown in FIG. 2.

We claim:

1. A method of detecting polynucleotide hybridization between a first polynucleotide and a second polynucleotide comprising the steps of:
    (a) detecting a first resonance frequency of a piezoelectric crystal having a first polynucleotide attached to a surface of said crystal;
    (b) exposing said attached first polynucleotide to a solution containing a separate source of a second polynucleotide for a sufficient length of time and under conditions suitable for hybridization to occur between said first polynucleotide and said second polynucleotide;
    (c) detecting a second resonance frequency of said crystal following said hybridization step while said crystal is still in contact with said solution containing said second polynucleotide; and
    (d) comparing said first and said second resonance frequencies.

2. The method of claim 1 wherein said second detection step is repeated over a period of time while hybridization is occurring.

3. The method of claim 1 further comprising raising the temperature on the surface of said crystal in order to remove said second polynucleotide and repeating the exposing, second detecting and comparing steps.

4. The method of claim 3 wherein said exposing, second detecting and comparing steps are repeated at least 5 times.

5. The method of claim 1 wherein said first polynucleotide is bonded to said crystal with a linker.

6. The method of claim 5 wherein said linker is an organic compound characterized by the presence of an azido group.

7. The method of claim 1 wherein said first polynucleotide is bonded to said crystal by a polymeric substrate.

8. The method of claim 10 wherein said polymeric substrate is selected from a class of polymers characterized by hydrolytically stable, hydrophobic backbones substituted with reactive pendant groups.

9. A method of detecting polynucleotide hybridization between a first polynucleotide and a second polynucleotide comprising the steps of:
    (a) detecting a first resonance frequency of a piezoelectric crystal having a first polynucleotide attached to a surface of said crystal;
    (b) exposing said attached first polynucleotide to a separate source of a second polynucleotide for a sufficient length of time and under conditions suitable for hybridization to occur between said first polynucleotide and said second polynucleotide;
    (c) washing said crystal to remove any excess source of said second polynucleotide and drying said crystal;
    (d) detecting a second resonance frequency of said crystal; and
    (e) comparing said first and said second resonance frequencies.

10. The method of claim 9 wherein said drying is performed under vacuum.

11. The method of claim 9 wherein said first polynucleotide is bonded to said crystal with a linker comprising an organic compound characterized by the presence of an azido group.

12. The method of claim 9 wherein said first polynucleotide is bonded to said crystal by a polymeric substrate.

13. A method of detecting DNA or RNA hybridization comprising the steps of:
   (a) detecting a first resonance frequency of a piezoelectric crystal having a first polynucleotide attached to a surface of said crystal;
   (b) exposing said crystal to a second source of DNA or RNA for a sufficient length of time and under conditions suitable for hybridization to occur;
   (c) rinsing excess solution form said crystal;
   (d) drying said crystal;
   (e) detecting a second resonance frequency of said crystal; and
   (f) comparing said first and second resonance frequencies.

14. A method of detecting DNA or RNA hybridization comprising the steps of:
   (a) detecting a first resonance frequency of a piezoelectric crystal having a first polynucleotide attached to a surface of said crystal;
   (b) exposing said crystal to a second source of DNA or RNA in solution for a sufficient length of time and under conditions suitable for hybridization to occur;
   (c) detecting a second resonance frequency of said crystal while it is still in said solution; and
   (d) comparing said first and said second resonance frequencies.

15. The method of claim 14 wherein said second detecting step is repeated over a period of time.

16. The method of claim 14 further comprising raising the temperature on the surface of said crystal in order to remove said second DNA or RNA and repeating the exposing, second detecting and comparing steps.

17. The method of claim 16 wherein said exposing, second detecting and comparing steps are repeated at least 5 times.

* * * * *

UNITED STATES PATENT AND TRADEMARK OFFICE
CERTIFICATE OF CORRECTION

PATENT NO.    :   5,945,280

DATED         :   August 31, 1999

INVENTOR(S)   :   Newton C. Fawcett, Jeffrey A. Evans and Naomi F. Campbell

It is certified that error appears in the above-identified patent and that said Letters Patent is hereby corrected as shown below:

In claim 8, first line, please delete "10" and insert -- 7 --

In claim 13, ninth line, please delete "form" and insert -- from --

Signed and Sealed this

Second Day of May, 2000

Attest:

Attesting Officer

Q. TODD DICKINSON

Director of Patents and Trademarks